United States Patent [19]

South

[11] Patent Number: 5,484,761

[45] Date of Patent: Jan. 16, 1996

[54] 5-METHOXY PYRIDINYLOXYPRIDAZINES, HERBICIDAL COMPOSITIONS AND USE THEREOF

[75] Inventor: Michael S. South, St. Louis, Mo.

[73] Assignee: Monsanto Company, St. Louis, Mo.

[21] Appl. No.: 320,488

[22] Filed: Oct. 11, 1994

[51] Int. Cl.[6] .................................................. A01V 43/58
[52] U.S. Cl. .................. 504/238; 544/238; 546/296; 546/303
[58] Field of Search ................ 504/238; 544/238

[56] References Cited

U.S. PATENT DOCUMENTS

| 3,427,146 | 11/1969 | Tamura et al. | 504/238 |
| 4,964,895 | 10/1990 | Moedritzer et al. | 548/376 |
| 5,240,940 | 8/1993 | Arnold et al. | 514/312 |

OTHER PUBLICATIONS

El–Abbady et al. Chem Abstr. vol. 112 entry 7708e (1990).
Barlin et al. Chem. Abstr. vol 111 entry 115193 (1989).
Rose et al. Chem. Abstr. vol. 75 entry 98525 )1971).

*Primary Examiner*—Donald G. Daus
*Attorney, Agent, or Firm*—Richard H. Shear; Joan Thierstein; Grace L. Bonner

[57] ABSTRACT

Disclosed are certain 5-methoxypyridinyloxypyridazines, compositions thereof which are herbicidal and methods of using such compositions for controlling undesired plants.

Intermediates useful in preparing the pyridinyloxypyridazines are also disclosed.

31 Claims, No Drawings

5-METHOXY PYRIDINYLOXYPRIDAZINES, HERBICIDAL COMPOSITIONS AND USE THEREOF

FIELD OF THE INVENTION

The present invention relates to novel compounds useful for controlling undesired plants and for retarding plant growth. More particularly, the present invention relates to certain pyridinyloxypyridazines useful for controlling undesired plants and for retarding plant growth.

PRIOR ART

In U.S. Pat. No. 4. 964,895, substituted 4-(4 -nitrophenoxy)pyrazoles have been disclosed as being useful as herbicides.

In U.S. Pat. No. 3,427,146, certain phenoxypyridazines have been disclosed as being useful as herbicides.

5-amino-4-chloro-2-phenylpyridizin-3-(2H)-one is a known pyridazinone herbicide and has the common name chloridazon.

4-Chloro-5-methylamino-2-($\alpha,\alpha,\alpha$-trifluoro-m-tolyl-)prisazine-3-(2H)-one is another known pyridazinone herbicide and has the common name norflurazon.

6-Chloro-3-phenylpyridazin-4-yl-S-octyl thiocarbonate is a known pyridazine herbicide and has the common name pyridate.

There is a continuing need in the art for herbicides which provide a broad spectrum of control of weeds and which may be better tolerated by crops. The present invention provides such kind of improved and useful herbicides.

SUMMARY OF THE INVENTION

The novel compounds of the present invention may be depicted by one of the following structural formulas:

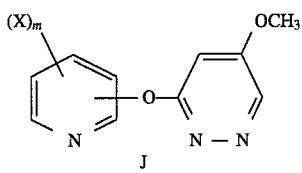

wherein:
X is $CF_3$, $OCF_2H$, $SCF_2H$, $OCH_2CF_3$, $OCH_2CF_2CF_2H$ or $OCH(CH_3)CF_3$.

The present invention provides novel compounds of the general Formula J depicted above which exhibit desirable herbicidal properties and further provides herbicidal compositions for the selective controlling of weeds in crop plants. The compositions comprise one or more compounds of Formula J herein by themselves or admixed with one or more carriers, such as solid and/or liquid inert extenders or diluents and/or wetting agents and optionally other active herbicides, insecticides, fungicides, safeners, growth regulators, plant nutrients and like additaments. The invention also provides an effective method of controlling undesirable plants, such as grasses, perennial and annual broadleafed weeds and so on which comprises applying to the locus of the plants to be controlled an effective amount of at least one pyridinyloxypyridazine to exert a herbicidal action.

These novel pyridinyloxypyridazine compounds which may be employed as an active ingredient in this invention can be prepared by a variety of new and useful processes, such as one of the general procedures as will be described below. Many of the depicted intermediate compounds are novel and useful for preparing the herbicidal pyridinyloxypyridazines herein.

DETAILED DESCRIPTION OF THE INVENTION

It has been shown that the pyridine oxygen-linked pyridazine compounds within the above depicted general Formula J are not only herbicidal against undesirable plants but also have good herbicidal tolerance by certain crop plants, especially corn. Novel compounds herein in many instances provide substantially equal or better herbicidal performance than the present widely commercially employed acetanilides but with better environmental acceptability. The preferred compounds herein provide a broader spectrum of weed control and show good perennial broadleaf activity. The field soil half-life of the preferred compounds provides longer residual control than alachlor but is short enough that any carryover problems are agronomically acceptable.

In this specification and claims, numerical values are not critical unless otherwise stated. That is, the numerical values may be read as if prefaced with the word "about" or "substantially".

The following defines the various terms used in the application.

The term "$C_1$–$C_{10}$ alkyl" or in the shortened form "$C_1$–$C_{10}$ alk" as used herein include the straight and branched aliphatic groups of one to ten carbon atoms, such as methyl, ethyl, propyl, isopropyl (1-methylethyl), butyl, isobutyl, (2-methylpropyl), sec-butyl, (1-methylpropyl), tert-butyl, (1,1-dimethylethyl), pentyl, isopentyl, (3-methylbutyl), sec-pentyl (1-methylbutyl), 1,1-dimethylpropyl, 1-2-dimethylpropyl, neopentyl, (2,2-dimethylpropyl), hexyl, isohexyl (4-methylpentyl), sec-hexyl, (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The terms, such as "$C_1$–$C_3$" and "$C_1$–$C_5$" are included in the term $C_1$–$C_{10}$ but with a corresponding lesser number of carbon atoms as indicated.

The term "$C_1$–$C_3$ haloalkyl" as used herein includes such radicals as trifluoromethyl, trichloromethyl, difluoromethyl, chlorodifluoromethyl, fluoromethyl, bromomethyl, pentafluoroethyl, heptafluoro-npropyl, pentachloroethyl, iodomethyl, etc., where the number of carbon atoms in the alkyl is 1–3, inclusive.

The term "halogen" either alone or in compound words such as "haloalky" denotes fluorine, chlorine, bromine or iodine.

The term "alkoxy" denotes methoxy, ethoxy, n-propyloxy, isopropyloxy and the different butoxy, pentoxy, hexoxy isomers, etc.

The term "alkenyl" denotes straight or branched alkenes, e.g., vinyl, 1-propenyl, 2-propenyl, and the different butenyl, pentenyl, hexenyl isomers, etc.

The term "alkynyl" denotes straight chain or branched alkynes, e.g., ethynyl, 1-propynyl, 2-propynyl, etc., including the different butynyl, pentynyl and hexynyl isomers.

The term "alkylthio" denotes methylthio, ethylthio and the various propylthio, butylthio, pentylthio and hexyithio isomers.

Alkylsulfinyl, alkylsulfonyl, alkylamine, etc., are defined analogously to the above terms.

A process for preparing the compounds of the present invention can be described in the following schematic diagrams which follow below.

The compounds according to this invention are suitably prepared by a variety of processes as will also be described below with greater particularity.

In broad aspect, the preferred overall process for preparing the compounds of Formula J is best viewed in the separate process steps required to prepare the necessary intermediates, immediate precursors and end products of the above formula. The products of "Processes I and II", provide the intermediates necessary for "Process III". The compounds according to Formula J are prepared by either a single process "III" or any combination of "Processes I-III". It is expressly understood that various modifications obvious to those skilled in the art are contemplated. Specific embodiments of the preparation of the compounds herein are described in Examples 1–3 below.

In the sequence of process steps described below, the various symbols defining radical substituents, e.g., X, Y, m, n, $R_1$–$R_2$, Rf, etc., have the same meaning as defined for the compounds of Formula J, unless otherwise qualified or limited.

Process I

This process describes the preparation of important intermediate compounds of Formula C which are useful in the overall process scheme for producing compounds of Formula J.

The first step in the process for the preparation of compounds of Formula J proceeds from either 2-halo-6-trifluoromethylpyridine or 2-halo-4-trifluoromethylpyridine A, which are commercially available. Treatment of Compound A with an appropriate salt of t-butyl alcohol chosen from potassium, sodium, or lithium gives a compound of Formula B. The reaction can be carried out in any non-reactive organic solvent, such as ether, tetrahydrofuran, benzene or t-butyl alcohol. The reaction temperatures may range from −78° C. to 150° C., preferably 0° C. to 100° C. The reaction period may be chosen from a few minutes to several weeks depending on the amounts of reagents, reaction temperature, etc. After the reaction is complete, the mixture containing the compounds of Formula B is diluted with water and extracted with an organic solvent. The organic solvent is then dried and evaporated in-vacuo.

The compounds of Formula B are utilized as is or if necessary the product is purified by standard methods such as crystallization or column chromatography.

Process I

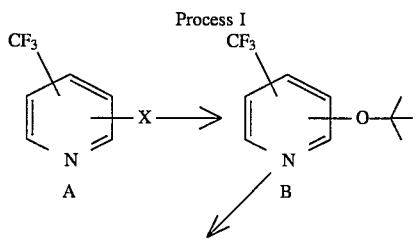

-continued

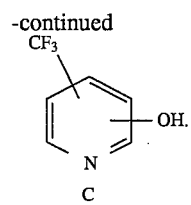

C

The second step in Process I involves the conversion of compounds of Formula B to C by treatment of B with an organic acid chosen from sulfonic acid, p-toluenesulfonic acid, acetic acid, or trifluoroacetic acid. The reaction may be carried out utilizing the organic acid as the solvent or in an organic solvent such as benzene, toluene, ether, methylene chloride, carbon tetrachloride or chloroform. The reaction temperature may range from −78° C. to 150° C., preferably 0° C. to 50° C.

Process II

This process describes the preparation of important intermediate compounds of Formula G which are useful in the overall process scheme for producing compounds of Formula J.

The first step in Process II involves the conversion of 4-benzyloxy-2-pyridone D which is known in the art (R. L. Shone, et al., *J. Heterocyclic Chem.*, 12, 389 (1975)) to compounds of Formula E. Compounds of Formula D are combined together with an appropriate base chosen from sodium hydroxide, potassium hydroxide or lithium hydroxide in water. An appropriate organic solvent is then added to this mixture chosen from carbon tetrachloride, benzene, dioxane or tetrahydrofuran. This two phase mixture is stirred vigorously while an excess of a halogenated methane chosen from $CF_2ClH$, $CF_2BrH$ or $CF_2IH$ is added slowly to this mixture to give compounds of Formula E. The mixture containing the compounds of Formula E are then diluted with an organic solvent and extracted several times with water. The compounds of Formula E are isolated by removal of the organic solvent in-vacuo and may be used as is or if necessary may be purified by standard methods such as crystallization or column chromatography.

Process II

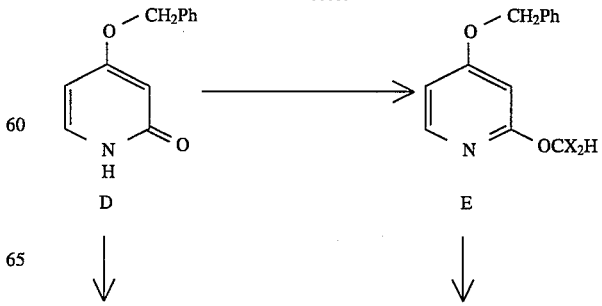

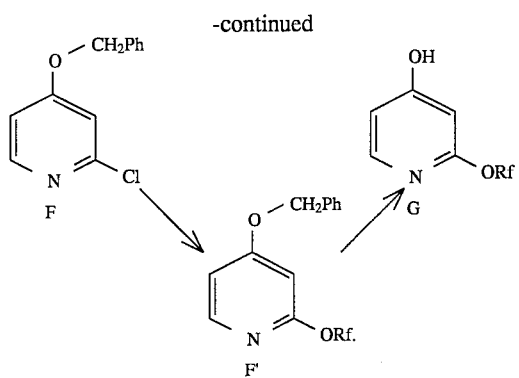

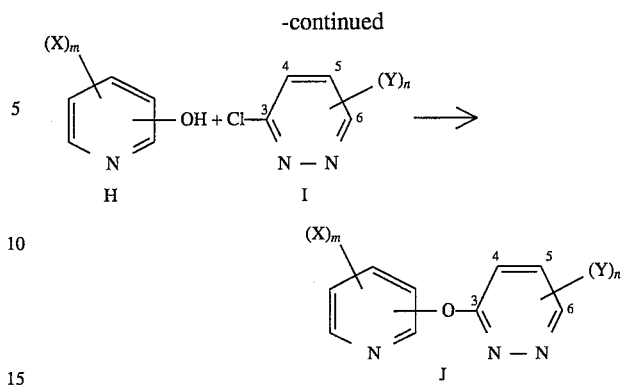

The second step in Process II involves the conversion of compounds of Formula E to G by treatment of E with hydrogen gas at a pressure from atmospheric to 0 kilo Pascals (kPa) and a catalyst chosen from Pd—C, Pt—C, or PtO$_2$ in an appropriate solvent chosen from benzene, methanol, ethanol or tetrahydrofuran.

An alternative method for preparing compounds of Formula G involves the conversion of compounds of Formula D to compounds of Formula F by treatment with a chlorinating agent chosen from SOCl$_2$, SO$_2$Cl$_2$, POCl$_3$, (CO)$_2$Cl$_2$ or PCl$_5$ either neat or in an appropriate organic solvent chosen from benzene, carbon tetrachloride, methylene chloride or chloroform. The compounds of Formula F are then treated with an appropriate fluorinated primary, secondary, or tertiary alcohol and a base chosen from NaH, lithium diisopropylamide or KH in an appropriate organic solvent chosen from dimethylsulfoxide, N,N-dimethylformamide, tetrahydrofuran or ether to give an intermediate compound 2-fluoroalkoxy-4-benzyloxypyridine, F'. The reaction temperature may range from −78° C. to 150° C. preferably 20° C. to 100° C. The reaction period may be chosen from a few minutes to several weeks depending on the amounts of reagents, reaction temperature, etc. The compounds of Formula F' are isolated by evaporation of the solvent followed by partitioning the crude product between an organic solvent and water. The organic solvent is then dried and evaporated in-vacuo. The compounds of Formula F' may be used as is or purified by standard methods such as crystallization or column chromatography. The compounds of Formula F' are then converted to compounds of Formula G by hydrogenation in a manner that is identical to that described above form the conversion of compounds of Formula E to compounds of Formula G.

Process III

This process describes the preparation of compounds of Formula J. Pyridinols of Formula H and pyridazines of Formula I, which are described in M. S. South, et. al., U.S. Patent application pending, are combined together with an appropriate base chosen from sodium hydride, potassium hydride, sodium bicarbonate, potassium carbonate, triethyl amine, N,N-diisopyropylethylamine, 2,6-lutidine, or DBU and optionally an appropriate catalyst chosen from TiCl$_4$, SnCl$_2$, FeCl$_3$CuCl, CuBr, AgBF$_4$ or CuF to give compounds of Formula J.

Process III

In these cases X$_m$ and Y$_n$ are defined as given above for Formula J. The reaction may be carried out in any anhydrous solvent or mixture of solvents, preferably ether, tetrahydrofuran, N,N-dimethylformamide, dimethylsulfoxide, diglyme, glyme, sulfolane, benzene, toluene or xylene. The reaction temperatures may range from −78° C. to 180° C., preferably 0° C. to 150°C. The reaction period may be chosen from a few minutes to several weeks depending on the amounts of reagents, reaction temperature, etc. The products of Formula J are isolated by diluting the reaction mixture with an organic solvent and extracting with water. The organic solvent is then removed in-vacuo and the products of Formula J are either used as is or purified by standard methods such as crystallization or chromatography, etc.

Preparation of some of the intermediates of the compounds of this invention and the compounds of this invention are illustrated by the following examples. In the examples which follow, all percentages are given on a weight basis unless otherwise indicated.

EXAMPLE 1

This example describes the preparation of 5-methoxy-3-[[6 -(trifluoromethyl)-2-pyridinyl]oxy]pyridazine, Compound No. 2, and is a specific embodiment of Process I and Process III.

A. 2-Chloro-6-trifluoromethylpyridine (5.0 g, 27.6 mmol) was dissolved in tert-butyl alcohol (135 mL). Potassium tert-butoxide (25.0 g, 220 mmol) was added and the mixture was refluxed under nitrogen for 20 h. After cooling, cold 3N HCl was carefully added to the flask until the pH was approximately 1–2. The resulting solution was extracted several times with methylene chloride. The organic layers were dried (MgSO$_4$) and evaporated. This residue was then treated with trifluoroacetic acid 1.5 mL) at 80° C. for 2 h. The solution was neutralized with aqueous sodium bicarbonate and extracted several times with methylene chloride. The organic layer was dried (MgSO$_4$), filtered and evaporated in-vacuo. The residue was recrystallized from methylene chloride and hexane to give 6-trifluoromethyl-2-pyridinol (2.8 g, 62% yield) as a white solid, mp=117° C. −118° C. Anal. Calcd. for C$_6$H$_4$NOF$_3$: C, 44.19; H, 2.47; N, 8.59

Found: C, 44.27; H, 2.43; N, 8.56

B. 6-Trifluoromethyl-2-pyridinol (2.0 g, 12.27 mmol), 2,6-lutidine (2.3 g, 21.5 mol) and 3 -chloro-5-methoxypyridazine (1.77 g, 12.27 mmol) were added to xylenes (30 Ml). The solution was refluxed under nitrogen for 17 h. After cooling, the solution was added to water and extracted three times with methylene chloride. The organic layer was dried (MgSO$_4$), filtered and evaporated in-vacuo. The crude product was purified by HPLC (1:1 ethyl acetate/methylene chloride) to give 5-methoxy-3-[6-(trifluoromethyl)-2-pyridinyl]oxy]pyridazine (1.5 g, 45% yield, Compound No. 2) as a light yellow oil, nD=1.5181.

EXAMPLE 2

This example describes the preparation of 3-[[2-(difluoromethoxy)-4pyridinyl]oxy]-5-methoxypyridazine, Example No. 5, and is a specific embodiment of Processes II and III.

A. 4-Benzyloxy-2-pyridone (311.4 g, 1.55 mol) was mechanically stirred under nitrogen in a mixture of dioxane (6.2 L) and 50% sodium hydroxide (2.48 L) while chlorodifluoromethane (1,332.4 g, 15.5 mol) was condensed into the 22 L flask over a 4 h period using a dry-ice condenser that was attached to one of the necks of the 4-neck flask. The temperature inside the flask was maintained below 35° C. by means of an ice-bath. The mixture was then stirred for 18 h maintaining the temperature of the mixture between 25° C. and 35° C. The dry-ice condenser was in place during the 18 h reaction time. The mixture was then diluted with water, acidified to pH 1 with conc. HCl and extracted three times with ethyl acetate. If emulsions formed the whole mixture was filtered through a bed of celite. The combined organic layers were dried (MgSO$_4$), filtered through silica gel and concentrated in-vacuo. The crude oil was chromatographed on a Prep-500 HPLC to give 2-difluoromethoxy-4-benzyloxypyridine (219.75 g, 56% yield) as a yellow oil, nD =1.5274. Anal. Calcd. for C$_{13}$H$_{11}$NO$_2$F$_2$: C,62.15; H,4.41; N,5.58 Found: C,62.18; H,4.40; N,5.52.

B. 2-Difluoromethoxy-4-benzyloxypyridine (219.75 g, 0.875 mol), ethanol (500 mL) and palladium on carbon (7.8 g, 5 mol %, 50% by weight water) were shaken on a Parr hydrogenator at 5393 kPa of hydrogen at RT for 2.5 h. The mixture was then filtered through celite and the solvent was evaporated in-vacuo. 2-Difluoromethoxy-4-hydroxypyridine (123 g, 87% yield) was obtained as a white solid after trituration with hexane, mp=88.6° C. –89.8° C. Anal. Calcd. for C$_6$H$_5$NO$_2$F$_2$: C,44.73; H,3.13; N,8.69 Found: C,44.82; H,3.13; N,8.76.

C. 2-Difluoromethoxy-4-hydroxypyridine (123 g, 0.764 mol), 3-chloro-5-methoxypyridazine (110.47 g, 0.764 mol), potassium carbonate (211.18 g, 1.53 mol), CuBr (54.80 g, 0.382 mol) and 18-crown-6 (1 g) were mechanically stirred under nitrogen in diglyme (1.28 L) at 100° C. for 30 h. The mixture was cooled to RT and partitioned between ethyl acetate and 2 L of 3% HCl. The layers were separated. The aqueous layer was then adjusted to pH—1 with conc. HCl and extracted twice with additional ethyl acetate. The combined organics were filtered through silica gel and then extracted twice with 1.5 N NaOH. Solids were formed which were removed by filtering the organic layer through silica gel and celite. The organic layer was dried (MgSO$_4$), filtered through silica gel and evaporated in-vacuo. The residue was triturated with ethyl acetate and filtered to give pure 3-[[2-(difluoromethoxy)-4-pyridinyl]oxy]-5-methoxypyridazine (92.5 g, 45% yield) as a light brown solid, mp=119° C. –120.5° C.

EXAMPLE 3

This example describes the preparation of 5-methoxy-3-[[2-(2,2,2-trifluoro-1-methylethoxy)-4pyridinyl]oxy]pyridazine, Compound No. 10 and is a specific embodiment of Processes II and III.

A. 4-Benzyloxy-2-pyridone (26.3 g, 0.131 mol) and POCl$_3$ (200 mL) was heated at reflux for 2 h. The mixture was cooled and poured into 1 L of crushed ice and then 500 mL of ethyl acetate was added. The mixture was treated with decolorizing carbon, filtered and then treated with solid potassium carbonate until gas ceased to evolve. The mixture was filtered and the layers were separated. The aqueous layer was extracted three times with ethyl acetate. The combined organic layers were treated with decolorizing carbon, dried (MgSO$_4$), filtered and the solvent was removed in-vacuo. The crude product was chromatographed to give 2-chloro-4-benzyloxypyridine (8 g, 28% yield) as a white solid, mp=91° C. –93° C. Anal. Calcd. for C$_{12}$H$_{10}$NO: C,65.61; H,4.59; N,6.38 Found: C,,65.59; H,4.55; N,6.39.

B. 2-Chloro-4-benzyloxypyridine (1.5 g, 6.85 mmol), 1,1,1-trifluoroisopropan-2-ol (1.56 g, 13.7 mmol) and NaH (0.33 g of 95%, 13.7 mmol) were stirred under nitrogen in DMF (30 mL) at 80° C. for 70 h. After 40 h additional portions (13.7 mmol each) of the alcohol and the NaH were added. The mixture was cooled to RT, poured into water and extracted several times with ethyl acetate. The organic layer was dried (MgSO$_4$), filtered and evaporated in-vacuo. The crude oil was chromatographed to give 4-(phenylmethoxy)-2-(2,2,2-trifluoro-1-methoxyethoxy)-pyridine (1.4 g, 69% yield) as a clear oil. Anal. Calcd. for C$_{15}$H$_4$NO$_2$F$_3$: C,60.61; H,4.75; N,4.71 Found: C,60.70; H,4.82; N,4.71.

C. 4-(Phenylmethoxy)-2-(2,2,2-trifluoro-1-methyloxy)-pyridine (1.19 g, 4 mmol) and palladium on carbon (5 mol %, 50% by weight water) in methanol (50 mL) were shaken on a Parr hydrogenator at 55 psi of hydrogen for 20 min. The mixture was filtered through celite and the solvent was evaporated in-vacuo. The crude material was purified by flash chromatography to give 2-(2,2,2-trifluoro-1-methylethoxy)-4-pyridinol (0.76 g, 92% yield) as a white solid, mp=67° C. –69° C. Anal. Calcd. for C$_8$H$_8$NO$_2$F$_3$: C,46.39; H,3.89; N,6.79 Found: C,46.37; H,3.89; N,6.68.

D. 2-(2,2,2-Trifluoro-1-methylethoxy)-4-pyridinol (0.64 g, 3.09 mmol), 3-chloro-5-methoxy-pyridazine (0.44 g, 3.09 mmol), potassium carbonate (0.85 g, 6.18 mmol) and CuBr (0.89 g, 6.18 mmol) were stirred under nitrogen in diglyme (5 mL) at 100° C. for 6 days. The mixture was then poured in water and extracted several times with ethyl acetate. The combined organic layers were dried (MgSO$_4$), filtered and evaporated in-vacuo. The crude product was purified by flash chromatography to give 5-methoxy-3-[[2-(2,2,2-trifluoro-1-methylethoxy)-4-pyridinyl]oxy]pyridazine (0.42 g, 43% yield, Compound No. 10) as a white solid, mp=100° C. –102° C.

Several other compounds of the present invention were prepared using generally the procedures illustrated above or other procedure obvious to one skilled in the art. Specific compounds illustrated of the present invention are given below where the prepared compounds are structurally depicted and named. Melting points and elemental analyses are provided for these compounds in the following table.

| CP NO. | Name | Structure | Analysis (%) Calc'd Found |
|---|---|---|---|
| 1 | PYRIDAZINE, 5-METHOXY-3-[[2-(TRIFLUOROMETHYL)-4-PYRIDINYL]OXY]- MP: 52.5–54.0 | 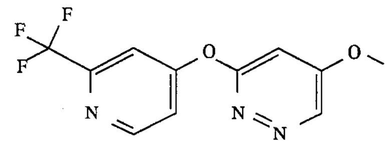 | C 48.72 48.59<br>H 2.97 2.92<br>N 15.49 15.46 |
| 2 | PYRIDAZINE, 5-METHOXY-3-[[6-(TRIFLUOROMETHYL)-2-PYRIDINYL]OXY]- | 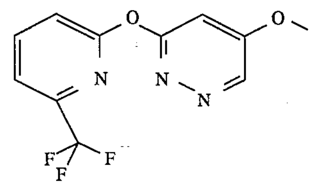 | C 48.72 48.59<br>H 2.97 2.99<br>N 15.49 15.41 |
| 3 | PYRIDAZINE, 5-METHOXY-3-[[5-(TRIFLUOROMETHYL)-3-PYRIDINYL]OXY]- | 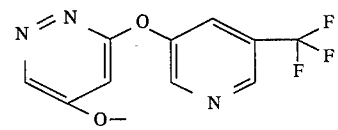 | |
| 4 | PYRIDAZINE, 5-METHOXY-3-[[4-(TRIFLUOROMETHYL)-2-PYRIDINYL]OXY]- | 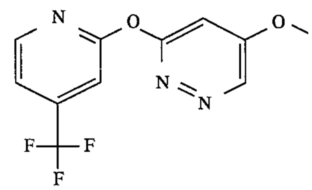 | C 47.95 47.93<br>H 3.29 3.11 |
| 5 | PYRIDAZINE, 3-[[2-(DIFLUOROMETHOXY)-4-PYRIDINYL]OXY]-5-METHOXY- MP: 119.0–120.5 | 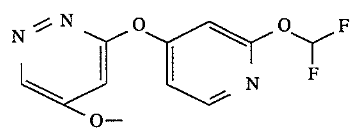 | |
| 6 | PYRIDAZINE, 3-[[6-(DIFLUOROMETHOXY)-2-PYRIDINYL]OXY]-5-METHOXY- | 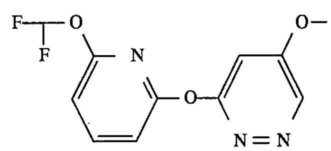 | C 49.08 49.34<br>H 3.37 3.45<br>N 15.61 15.39 |
| 7 | PYRIDAZINE, 3-[[2-((DIFLUOROMETHYL)THIO]-4-PYRIDINYL]OXY]-5-METHOXY- MP: 96.0–97.0 | 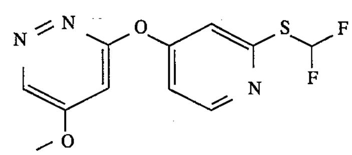 | C 46.31 46.32<br>H 3.18 3.17<br>N 14.73 14.71 |
| 8 | PYRIDAZINE, 5-METHOXY-3-[[2-(2,2,2-TRIFLUOROETHOXY)-4-PYRIDINYL]OXY]- MP: 75.0–76.0 | 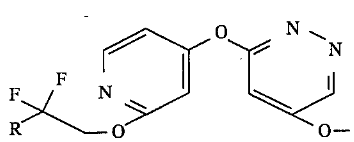 | C 47.85 47.79<br>H 3.35 3.35<br>N 13.95 13.99 |
| 9 | PYRIDAZINE, 5-METHOXY-3[[2-(2,2,3,3-TETRAFLUOROPROPOXY)-4-PYRIDINYL]OXY]- MP: 48.0–50.0 | 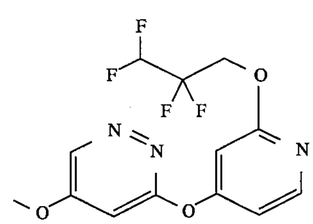 | C 46.86 47.01<br>H 3.33 3.42<br>N 12.61 12.53 |

-continued

| CP NO. | Name | Structure | Analysis (%) Calc'd Found |
|---|---|---|---|
| 10 | PYRIDAZINE, 5-METHOXY-3-[[2-(2,2,2-TRIFLUORO-1-METHYLETH-OXY)-4-PYRIDINYL]OXY]- MP: 100.0–102.0 | 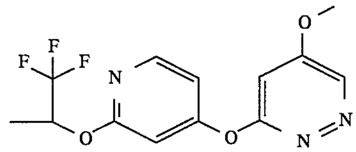 | C 49.53  49.55<br>H 3.84  3.83<br>N 13.33  13.30 |

PRE-EMERGENT ACTIVITY ON PLANTS

As noted above, compounds of this invention have been found to be effective as herbicides, particularly as pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The symbol C represents complete control and N or a hyphen represents no data.

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha) or other rate as indicated in Table A. After treatment, the pans were moved to a greenhouse bench where they were watered as needed to give adequate moisture for germination and growth.

Approximately 10–14 days (usually 11 days) after planting and treating, the plants were observed and the results recorded.

The plant species usually regarded as weeds which were utilized in one set of pre-emergent activity tests, the data for which are shown in Table A, are identified by letter headings printed above the columns according to the following legend:

COBU-Cocklebur
VELE-Velvetleaf
DOBR-Downy Brome
MOGL-Morningglory
BYGR-Barnyardgrass
ANBG-Annual Bluegrass
SEJG-Seedling Johnsongrass *
YENS-Yellow Nutsedge
INMU-Indian Mustard
WIBW-Wild Buckwheat
COTT-Cotton
RICE-Rice
SOYB-Soybean
CORN-Corn
WHEA-Wheat
JGRZ-Johnsongrass, Rhizome
CNTH-Canadian Thistle
QGRZ-Quackgrass, Rhizome
FOXT-Foxtail, Green
CWBS-Catchweed Bedstream
RAPE-Rape
CHWD-Chickweed, Common
WDOA-Wild Oats
BLGR-Blackgrass
RUTH-Russian Thistle
FDBW-Field Bindweed
CBGR-Crabgrass, Large
BISW-Birdseye Speedwell
BARL-Barley \* Grown from vegetative propagules

TABLE A

| CP NO. | Rate Kg/Ha | COTT | RICE | SOYB | CORN | WHEA | JBRZ | YENS | CNTH | FDBW | QGRZ |
|---|---|---|---|---|---|---|---|---|---|---|---|
| 1 | 5.6 | 100 | 99 | 99 | 100 | 100 | 98 | 98 | 99 | 100 | 98 |
| 1 | 1.1 | 100 | 50 | 98 | 100 | 100 | 40 | 90 | 98 | 100 | 98 |
| 1 | 0.28 | 30 | 15 | 95 | 97 | 20 | 5 | 70 | 95 | 99 | 95 |
| 1 | 0.07 | 5 | 5 | 40 | 0 | 5 | 0 | 10 | 40 | 99 | 5 |

| CP NO. | Rate Kg/Ha | FOXT | CWBG | RAPE | WHEA | WDOA | DOBR | BLGR | WIBW | RUTH | CHWD | BISW | CWBG |
|---|---|---|---|---|---|---|---|---|---|---|---|---|---|
| 1 | 0.07 | 90 | 90 | 90 | 0 | 10 | 0 | 15 | 40 | 15 | 95 | — | — |
| 1 | 0.004 | 10 | 30 | 25 | 0 | 0 | 0 | 0 | 40 | 0 | 80 | — | — |
| 2 | 0.07 | 20 | 0 | 20 | 0 | 0 | 0 | 30 | — | — | — | — | — |
| 2 | 0.017 | 0 | 0 | 0 | 0 | 0 | 0 | 0 | 0 | 0 | 0 | 0 | 0 |
| 5 | | | | | 75 | 35 | 35 | 75 | 75 | 35 | 99 | — | — |
| 5 | 0.017 | 25 | 75 | 30 | 0 | 20 | 30 | 20 | 30 | 0 | 85 | — | — |

TABLE A-continued

| | | | | | | | | | | | | | |
|---|---|---|---|---|---|---|---|---|---|---|---|---|---|
| 5 | 0.004 | 20 | 30 | 0 | 0 | 0 | 0 | 5 | 15 | 0 | 75 | — | — |
| 5 | 0.28 | 100 | — | 65 | 25 | 35 | 30 | 100 | — | — | 100 | 100 | 100 |
| 5 | 0.14 | 100 | — | 75 | 15 | 35 | 35 | 98 | — | — | 100 | 100 | 95 |

| CP NO. | Rate Kg/Ha | YENS | ANBG | SEJG | DOBR | BYGL | MOGL | COBW | VELE | INMU | WIBW |
|---|---|---|---|---|---|---|---|---|---|---|---|
| 1 | 1.12 | 100 | 100 | 100 | 100 | 100 | 100 | 90 | 100 | 100 | 100 |
| 2 | 1.12 | 20 | 70 | 50 | 30 | 80 | 70 | 20 | 70 | 100 | 80 |
| 3 | 1.12 | 0 | 30 | 20 | 20 | 50 | 70 | 0 | 40 | 80 | 30 |
| 4 | 2.24 | 0 | 10 | 0 | 0 | 0 | 0 | 0 | 0 | 20 | 20 |
| 5 | 11.2 | 80 | 100 | 90 | 100 | 100 | 80 | 70 | 100 | 90 | 90 |

| CP NO. | Rate Kg/Ha | CBGR | SEJG | RICE | SOYA | CORN | BYGR | COTT | VELE | MOGL | COBW |
|---|---|---|---|---|---|---|---|---|---|---|---|
| 2 | 1.12 | 95 | 90 | 30 | 25 | 0 | 70 | 0 | 30 | 75 | 10 |
| 2 | 0.28 | 90 | 10 | 0 | 5 | 0 | 50 | 0 | 20 | 35 | 0 |

| CP NO. | Rate Kg/Ha | FOXT | YENS | BYGR | RICE | CORN | VELE | MOGL | COBW | SOYB |
|---|---|---|---|---|---|---|---|---|---|---|
| 6 | 1.0 | 100 | 0 | 0 | 5 | 0 | 100 | 70 | 0 | 20 |
|   | 0.2 | 0 | 0 | 0 | 10 | 0 | 15 | 0 | 0 | 10 |

| CP NO. | Rate Kg/Ha | RAPE | WHEA | WIBW | BARL | CHWD | DOBR | CWBS | BYGR | FOXT | WDOA |
|---|---|---|---|---|---|---|---|---|---|---|---|
| 7 | 1.12 | 100 | 30 | 99 | 40 | — | 85 | 98 | 99 | 100 | 100 |
| 8 | 1.12 | 100 | 20 | 98 | 25 | — | 75 | 100 | 99 | 104 | 45 |
| 9 | 1.12 | 100 | 98 | 99 | 90 | 100 | 100 | 100 | 99 | 100 | — |
| 10 | 1.12 | 100 | 95 | 99 | 90 | — | 100 | 99 | 100 | 100 | 85 |

POST-EMERGENT HERBICIDE ACTIVITY ON PLANTS

Although, as has been stated above, the compounds of this invention exhibit predominantly preemergence activity in greenhouse testing, nevertheless many of these compounds are active post-emergent herbicides. The post-emergent activity is best seen on younger plants treated at the 1½ to 2 leaf stage. In the tests which follow, larger and more developed plants were used.

The post-emergence herbicidal activity of compounds of this invention was demonstrated by greenhouse testing, and the results are shown in the following Table B.

Top soil was placed in pans having holes in the bottom and compacted to a depth of 0.95 to 1.27 cm from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha or other rate as indicated in Table B while applying a total amount of solution or suspension equivalent to 1870 L/ha. The pans were returned to the greenhouse and watered as before and the injury to the plants as compared to those in control pans was observed at approximately 10–14 days (usually 11 days). The plant identifying codes and symbols in Table A are the same as above defined.

TABLE B

| CP NO. | Rate Kg/Ha | YENS | ANBG | SEJG | DOBR | BYGR | MOGL | COBU | VELE | INMU | WIBW |
|---|---|---|---|---|---|---|---|---|---|---|---|
| 1 | 1.12 | 30 | 60 | 60 | 30 | 50 | 70 | 60 | 80 | 70 | 90 |
| 2 | 1.12 | 0 | 0 | 0 | 0 | 30 | 20 | 20 | 40 | 50 | 40 |
| 3 | 1.12 | 0 | 0 | 0 | 0 | 0 | 20 | 20 | 20 | 20 | 0 |
| 4 | 2.24 | 0 | 0 | 0 | 40 | 0 | 20 | 0 | 20 | 10 | 0 |
| 5 | 11.1 | 50 | 80 | 60 | 40 | 70 | 70 | 50 | 60 | 80 | 90 |

| CP NO. | RATE Kg/Ha | FOXT | YENS | BNGR | RICE | CORN | VELE | MOGL | COBU | SOYB |
|---|---|---|---|---|---|---|---|---|---|---|
| 6 | 1.0 | 0 | 0 | 0 | 0 | 5 | 55 | 45 | 25 | 25 |

| CP NO. | RATE Kg/Ha | RAPE | WHEA | WIBW | BARL | CHWD | DOBR | CWBS | BLGR | FOXT | WDOA |
|---|---|---|---|---|---|---|---|---|---|---|---|

TABLE B-continued

| 9  | 1.12 | 99 | 20 | 99 | 30 | 95 | 60 | 95 | 95 | 95 | 80 |
| 10 | 0.28 | 99 | 15 | 15 | 15 | 35 | 90 | 90 | 95 | 70 | 45 |

As can be seen from the data above, some of the compounds are suitably safe on certain crops and can thus be used for selective control of weeds in these crops. Known safeners can be added to the formulated herbicidal formulation when additional crop safening is indicated.

The methods of making such compositions are well known. Solutions are prepared by simply mixing the ingredients to be included therein. Fine solid compositions are made by blending and, usually, grinding as in a hammer or fluid energy mill. Suspensions are prepared by wet milling, for example. Granules and pellets can be made by spraying the material containing the active material upon preformed granular carriers or by agglomeration techniques or the like.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenyl) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 paints) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsions of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include N,N-dimethylformamide, dimethylsulfoxide, N-methyl-pyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite clay for heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives

2-Chloro-4-ethylamino-6-isopropylamino-s-triazine

2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1,2,4-triazole
6,7-Dihydrodipyrido (1,2-d:α', 1'-c)-pyrazidiinium salt
5-Bromo-3-isopropyl-6-methyluracil 1,1'-dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl) nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N'-(3-chloro-4-methylphenyl) urea
3-(3,4-Dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
-Chloro-N[(4-methoxy-6-methyl-3,5-triazin-2-yl)aminocarbonyl]-benzenesulfonamide
Methyl-2-(((((4,6-dimethyl-2-pyrimidinyl)amino)carbonyl)amino)sulfonyl)amino)sulfonyl) benzoate
Ethyl 2-[methyl-2-(((((4,6-dimethyl-2-pyrimidinyl)amino)carbonyl)amino)sulfonyl)]benzoate
Methyl-2 ((4,6-dimethoxy pyrimidin-2-yl ) aminocarbonyl)amino sulfonyl methyl) benzoate
Methyl 2-(((((4-methoxy-6-methyl-1,3,5-triazin-2yl)amino)carbonyl)amino)sulfonyl) benzoate Carbamates/Thiolcarbamates 2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-Propyl N,N-dipropylthiolcarbamate
S-2,3,3-Trichloroallyl N,N-diisopropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfony]amino]phenyl]acetamide N-isopropyl-2-chloroacetanilide
2',6'-Diethyl-N-methoxymethyl-2-chloroacetanilide (aka alachlor)
2'-Methyl-6'-ethyl-N-(2-methoxypropyl-2-yl)-2-chloroacetanilide
α,α,α, -Trifluoro-2,6-dinitro-N,N-dipropyl-p-toluidine
N-(1,1-dimethylpropynyl)-3,5-dichlorobenzamide
2-Chloro-N-ethoxymethyl-6'-ethylacet-o-toluidide (aka acetochlor)
2-Chloro-6'-ethyl-N-(2-methoxy-1-methylethyl)acet-o-toluidide (aka as metolachlor)
2-Chloro-N-isopropylacetanilide (aka as propachlor)
S-4-Chloro-N-isopropylcarbaniloylmethyl-O,O-dimethyl phosphorothioate (aka anilofos)
N-Butoxymethyl-2-chloro-2',6'-diethylacetanilide (aka butachlor)
3-(4-Bromo-3-chlorophenyl)-1-methoxy-1-methylurea (aka chlorobromuron)

N-Chloroacetyl-N-(2,6-diethylphenyl)glycine (aka diethatyl)
2-Chloro-N-(2-methoxyethyl)acet-2',6', -xylidide (aka dimethachlor)

Preferred are herbicide mixtures of the 3-pyrazolyloxypyridazine and one or more of a just-mentioned 2-chloroacetanilides. Especially, preferred 2-chloroacetanilides include acetochlor, alachlor, butachlor and metolachlor. The preferred ratio of pyridazine to 2-chloroacetanilide is between 10:1 and 1:10.

Acids/Esters/Alcohols 2,2-Dichloropropionic acid
2-Methyl-4-chlorophenoxyacetic acid
2-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts
Butyl 2-[4-[[5-(trifluoromethyl)-2-pyridinyl]oxy]-phenoxy] propanoate Ethers 2,4-Dichlorophenyl-4-nitrophenyl ether
2-Chloro-α,α,α-trifluoro-p-tolyl-3-ethoxy-4-nitrodiphenyl ether
5-(2-Chloro-4-trifluoromethylphenoxy)-N-methyl sulfonyl-2-nitrobenzamide
1'-(Carboethoxy) ethyl 5-[2-chloro-4-(trifluoromethyl)phenoxy]-2 -nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-Oxabicyclo (2.2.1) heptane, 1-methyl-4-(1-methylphenylmethoxy)-, exo Fertilizers useful in combination with the active ingredients include, for example, ammonium nitrate, urea, potash and superphosphate. Other useful additaments include materials in which plant organisms take root and grow such as compost, manure, humus, sand and the like.

It is common practice to use various antidotal or safening compounds to reduce the phytotoxicity of certain herbicides to various crops, especially corn. Accordingly, together with the 3-pyrazolyl-oxypyridazines of the present invention, alone or in combination with a herbicidal 2-chloroacetanilide, one can include in the formulations a safening amount of a suitable antidotal compound. Among suitable safeners for inclusion in the formulations of the present invention are fluorazole, cyometrinal, oxabetrinil, dichlormid, AD-67, 1,3-oxazolidine dichloroacetamides and other compounds known in the art as antidotes for herbicides, especially for corn one preferred safener is 3-(dichloroacetyl)-5-(2-furanyl)-(2,2-dimethyl oxazolidine.

Herbicidal formulations of the types described above are exemplified in several illustrative embodiments below.

|  | Weight Percent |
| --- | --- |
| I. Emulsifiable Concentrates | |
| A. Compound of Example No. 1 | 11.0 |
| Free acid of complex organic phosphate or aromatic or aliphatic hydrophobe base (e.g., GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 76.96 |
|  | 100.00 |
| B. Compound of Example No. 2 | 25.00 |
| Free acid of complex organic phosphate or aromatic or aliphatic hydrophobe base (e.g., GAFAC RE-610) | 5.00 |
| Polyoxyethylene/polyoxyproplene block copolymer with butanol (e.g., Tergitol XH) | 1.60 |
| Phenol | 4.75 |
| Monochlorobenzene | 63.65 |
|  | 100.00 |
| II. Flowables | |
| A. Compound of Example No. 3 | 25.00 |
| Methyl cellulose | 0.3 |
| Silica Aerogel | 1.5 |
| Sodium lignosulfonate | 3.5 |
| Sodium N-methyl-N-oleyl taurate | 2.0 |
| Water | 67.7 |
|  | 100.00 |
| B. Compound of Example No. 4 | 45.0 |
| Methyl cellulose | 0.3 |
| Silica aerogel | 1.5 |
| Sodium lignosulfonate | 3.5 |
| Sodium N-methyl-N-oleyl taurate | 2.0 |
| Water | 47.7 |
|  | 100.00 |
| III. Wettable Powders | |
| A. Compound of Example No. 5 | 25.0 |
| Sodium lignosulfonate | 3.0 |
| Sodium N-methyl-N-oleyl-taurate | 1.0 |
| Amorphous silica (synthetic) | 71.0 |
|  | 100.00 |
| B. Compound of Example 6 | 80.00 |
| Sodium dioctyl sulfonsuccinate | 1.25 |
| Calcium lignosulfonate | 2.75 |
| Amorphous silica (synthetic) | 16.00 |
|  | 100.00 |
| C. Compound of Example No. 7 | 10.0 |
| Sodium lignosulfonate | 3.0 |
| Sodium N-methyl-N-oleyl-taurate | 1.0 |
| Kaolinite clay | 86.0 |
|  | 100.00 |
| IV. Dusts | |
| A. Compound of Example No. 8 | 2.0 |
| Attapulgite clay | 98.0 |
|  | 100.00 |
| B. Compound of Example No. 9 | 60.0 |
| Montmorillonite | 40.0 |
|  | 100.00 |
| C. Compound of Example No. 10 | 30.0 |
| Ethylene glycol | 1.0 |
| Bentonite | 69.0 |
|  | 100.00 |
| D. Compound of Example No. 13 | 1.0 |
| Diatomaceous earth | 99.0 |
|  | 100.00 |
| V. Granules | |
| A. Compound of Example No. 1 | 15.0 |
| Granular attapulgite (20/40 mesh) | 85.0 |
|  | 100.00 |
| B. Compound of Example No. 2 | 30.0 |
| Diatomaceous earth (20/40) | 70.0 |
|  | 100.00 |
| C. Compound of Example No. 3 | 1.0 |
| Ethylene glycol | 5.0 |
| Methylene blue | 0.1 |
| Pyrophyllite | 93.9 |
|  | 100.00 |
| D. Compound of Example No. 4 | 5.0 |
| Pyrophyllite (20/40 | 95.0 |
|  | 100.00 |

When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some .instances. One skilled in the art can readily determine from this specification, including the above examples, the optimum rate to be applied in any particular case.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A compound having the chemical structure

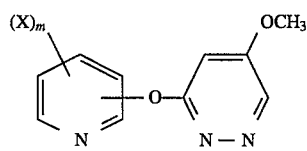

wherein X is $CF_3$, $OCF_2H$, $SCF_2H$, $OCH_2CF_3$, $OCH_2CF_2CF_2H$, or $OCH(CH_3)CF_3$ and m is an integer of 1, 2 or 3.

2. 5-Methoxy-3-[[2-(trifluoromethyl)-4-pyridinyl]oxy]pyridazine.

3. 5-Methoxy-3-[[6-(trifluoromethyl)-2-pyridinyl]oxy]pyridazine.

4. 5-Methoxy-3-[[5-(trifluoromethyl)-3-pyridinyl]oxy]pyridazine.

5. 5-Methoxy-3-[[4-(trifluoromethyl)-2-pyridinyl]oxy]pyridazine.

6. 3-[[2-(Difluoromethoxy)-4-pyridinyl]oxy]-5-methoxypyridazine.

7. 3-[[6-Difluoromethoxy)-2-pyridinyl]oxy]-5-methoxypyridazine.

8. 3-[[2-(Difluoromethylthio)-4-pyridinyl]-oxy]-5-methoxypyridazine.

9. 5-Methoxy-3-[[2-(2,2,2-trifluoroethoxy)-4-pyridinyl]oxy]pyridazine.

10. 5-Methoxy-3-[[2-(2,2,3,3-tetrafluoropropoxy)-4-pyridinyl]oxy]pyridazine.

11. 5-Methoxy-3-[[2-(2,2,2-trifluoro-1-methylethoxy)-4-pyridinyl]oxy]puridazine.

12. A herbicidal composition containing a carrier and a compound having the chemical structure

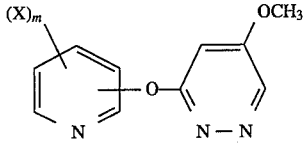

wherein X is $CF_3$, $OCF_2H$, $SCF_2H$, $OCH_2CF_3$, $OCH_2CF_3$, $OCH_2CF_2CF_2H$ or $OCH(CH_3)CF_3$, and m is an integer of 1, 2 or 3.

13. The composition of claim 12 wherein the compound is 5-Methoxy-3-[[2-(trifluoromethyl)-4-pyridinyl]oxy]pyridazine.

14. The composition of claim 12 wherein the compound is 5-Methoxy-3-[[6-(trifluoromethyl)-2-pyridinyl]oxy]pyridazine.

15. The composition of claim 12 wherein the compound is 5-Methoxy-3-[[5-(trifluoromethyl)-3-pyridinyl]oxy]pyrdiazine.

16. The composition of claim 12 wherein the compound is 5-Methoxy-3-[[4-(trifluoromethyl)-2-pyridinyl]oxy]pyrdiazine.

17. The composition of claim 12 wherein the compound is 3-[[2-(Difluoromethoxy)-4-pyridinyl]oxy]-5-methoxypyridazine.

18. The composition of claim 12 wherein the compound is 3-[[6-Difluoromethoxy)-2-pyridinyl]oxy]-5-methoxypyridazine.

19. The composition of claim 12 wherein the compound is 3-[[2-(Difluoromethylthio)-4-pyridinyl]-oxy]-5-methoxypyridazine.

20. The composition of claim 12 wherein the compound is 5-Methoxy-3-[[2-(2,2,2-trifluoroethoxy)-4-pyridinyl]oxy]pyridazine.

21. The composition of claim 12 wherein the compound is 5-Methoxy-3-[[2-(2,2,3,3-tetrafluoropropoxy)-4-pyridinyl]oxy]pyridazine.

22. A herbicidal method comprising applying to a plant locus a herbicidally-effective amount of a compound having the chemical structural formula or an agriculturally acceptable salt thereof

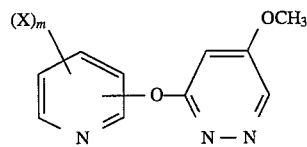

wherein X is $CF_3$, $OCF_2H$, $SCF_2H$, $OCH_2CF_3$, $OCH_2CF_2$, $CF_2H$ or $OCH(CH_3)CF_3$ and m is an integer of 1, 2 or 3.

23. The method according to claim 22 wherein the compound is 5-Methoxy-3-[[2-(trifluoromethyl)-4-pyridinyl]oxy]pyridazine.

24. The method according to claim 22 wherein the compound is 5-Methoxy-3-[[6-(trifluoromethyl)-2-pyridinyl]oxy]pyridazine.

25. The method according to claim 22 wherein the compound is 5-Methoxy-3-[[5-(trifluoromethyl)-3-pyridinyl]oxy]pyridazine.

26. The method according to claim 22 wherein the compound is 5-Methoxy-3-[[4-(trifluoromethyl)-2-pyridinyl]oxy]pyridazine.

27. The method according to claim 22 wherein the compound is 3-[[2-(Difluoromethoxy)-4-pyridinyl]oxy]-5-methoxypyridazine.

28. The method according to claim 22 wherein the compound is 3-[[6-Difluoromethoxy)-2-pyridinyl]oxy]-5-methoxypyridazine.

29. The method according to claim 22 wherein the compound is 3-[[2-(Difluoromethylthio)-4-pyridinyl]oxy]-5-methoxyridazine.

30. The method according to claim 22 wherein the compound is 5-Methoxy-3-[[2-(2,2,2-trifluoroethoxy)-4-pyridinyl]oxy]pyridazine.

31. The method according to claim 22 wherein the compound is 5-Methoxy-3-[[2-(2,2,3,3-tetrafluoropropoxy)-4-pyridinyl]oxy]pyridazine.

\* \* \* \* \*